United States Patent
Kapadia

(10) Patent No.: US 12,426,971 B2
(45) Date of Patent: Sep. 30, 2025

(54) SURGICAL ROBOTIC SYSTEMS

(71) Applicant: Covidien LP, Mansfield, MA (US)

(72) Inventor: Jaimeen Kapadia, Cambridge, MA (US)

(73) Assignee: Covidien LP, Mansfield, MA (US)

( * ) Notice: Subject to any disclaimer, the term of this patent is extended or adjusted under 35 U.S.C. 154(b) by 478 days.

(21) Appl. No.: 17/788,434

(22) PCT Filed: Dec. 21, 2020

(86) PCT No.: PCT/US2020/066303
§ 371 (c)(1),
(2) Date: Jun. 23, 2022

(87) PCT Pub. No.: WO2021/150334
PCT Pub. Date: Jul. 29, 2021

(65) Prior Publication Data
US 2023/0035946 A1    Feb. 2, 2023

Related U.S. Application Data

(60) Provisional application No. 62/965,366, filed on Jan. 24, 2020.

(51) Int. Cl.
  *A61B 34/37*   (2016.01)
  *A61B 17/00*   (2006.01)
  *A61B 17/34*   (2006.01)
  *A61B 34/30*   (2016.01)

(52) U.S. Cl.
  CPC .... *A61B 34/37* (2016.02); *A61B 2017/00477* (2013.01); *A61B 17/3421* (2013.01); *A61B 2034/302* (2016.02)

(58) Field of Classification Search
  USPC .......................................................... 606/1
  See application file for complete search history.

(56) References Cited

U.S. PATENT DOCUMENTS

| 5,942,737 | A | * | 8/1999 | Waters | H01M 50/249 200/50.28 |
| 8,828,023 | B2 | | 9/2014 | Neff et al. | |
| 9,757,149 | B2 | | 9/2017 | Cooper et al. | |
| 2016/0000512 | A1 | * | 1/2016 | Gombert | A61B 34/30 606/130 |

(Continued)

FOREIGN PATENT DOCUMENTS

| WO | WO-2013075205 A1 * | 5/2013 | ......... A61B 17/3403 |
| WO | 2017205467 A1 | 11/2017 | |
| WO | 2019136062 A1 | 7/2019 | |

OTHER PUBLICATIONS

International Search Report wnd Written Opinion dated Mar. 22, 2021, issued in corresponding international application No. PCT/US2020/066303, 13 pages.

*Primary Examiner* — Jennifer Pitrak McDonald
*Assistant Examiner* — Michael T. Holtzclaw
(74) *Attorney, Agent, or Firm* — Carter, DeLuca & Farrell LLP

(57) ABSTRACT

A surgical robotic arm for use in a minimally invasive surgical procedure includes an elongated rail configured for slidable engagement of a surgical instrument, and a trocar mount disposed at an end portion of the rail. The trocar mount is rotatable relative to the end portion of the rail to assist with loading and unloading the surgical instrument.

18 Claims, 5 Drawing Sheets

(56) References Cited

U.S. PATENT DOCUMENTS

2017/0086927 A1\* 3/2017 Auld ................. A61B 34/30
2018/0318020 A1 11/2018 Thompson et al.
2019/0159851 A1 5/2019 Karguth et al.
2020/0405417 A1\* 12/2020 Shelton, IV ......... A61B 90/361

\* cited by examiner

SURGICAL ROBOTIC SYSTEMS

FIELD

The present technology is generally related to robotic surgical systems used in minimally invasive medical procedures.

BACKGROUND

Some robotic surgical systems included a console supporting a surgical robotic arm and a surgical instrument or at least one end effector (e.g., forceps or a grasping tool) mounted to the robotic arm. The robotic arm provided mechanical power to the surgical instrument for its operation and movement. Each robotic arm may have included an instrument drive unit operatively connected to the surgical instrument.

The instrument drive unit was typically coupled to the robotic arm via a rail. The rail allowed the instrument drive unit and the attached surgical instrument to move along an axis of the rail, providing a means for adjusting the axial position of the end effector of the surgical instrument.

SUMMARY

In one aspect of the present disclosure, a surgical robotic arm for use in a minimally invasive surgical procedure includes a plurality of elongate members movably coupled to one another and an elongated rail pivotably coupled to at least one of the elongate members. The rail has a proximal end portion, a distal end portion, and a track defined between the proximal and distal end portions. The rail is configured for slidable engagement of a surgical instrument. A trocar mount is disposed at the distal end portion of the rail and defines an opening configured to receive at least one of a trocar or an elongated shaft of the surgical instrument. The trocar mount is configured to rotate relative to the distal end portion of the rail.

In aspects, the opening of the trocar mount may define an axis therethrough along which the surgical instrument is configured to translate.

In aspects, the trocar mount may be configured to rotate relative to the distal end portion of the rail between a first position and a second position. In the first position, the axis of the opening of the trocar mount is parallel with a longitudinal axis defined by the track of the rail. In the second position, the axis of the opening of the trocar mount is disposed at a non-parallel angle relative to the longitudinal axis of the track of the rail.

In aspects, the trocar mount may include a back member and a pair of clamp arms extending from the back member. The clamp arms may together define the opening of the trocar mount.

In aspects, the trocar mount may further include a button attached to the back member. The button may be configured to move between an unactuated position, in which the button locks the trocar mount in the first position, and an actuated position, in which the trocar mount is free to rotate relative to the distal end portion of the rail.

In aspects, the button may be resiliently biased toward the unactuated position.

In aspects, the distal end portion of the rail may define a pocket having the back member of the trocar member movably received therein.

In aspects, the back member of the trocar mount may be pivotably coupled to the distal end portion of the rail.

In aspects, the elongate members may include: a first elongate member having a first end and a second end; a second elongate member having a first end rotatably connected to the second end of the first elongate member, and a second end; and a third elongate member having a first end rotatably connected to the second end of the second elongate member, and a second end. The distal end portion of the rail may be rotatably coupled to the second end of the third elongate member.

In accordance with another aspect of the disclosure, a surgical robotic system is provided and includes an elongated rail, an instrument drive unit, a surgical instrument, and a trocar mount. The rail has a proximal end portion, a distal end portion, and a track defined between the proximal and distal end portions. The instrument drive unit is configured for slidable engagement with the track of the rail. The surgical instrument includes a housing portion configured to detachably connect to the instrument drive unit, an elongate shaft extending distally from the housing portion, and an end effector coupled to a distal end portion of the elongate shaft. The instrument drive unit is configured to drive an operation of the end effector of the surgical instrument. The trocar mount is rotatably coupled to the distal end portion of the rail and defining an opening configured to receive the elongate shaft of the surgical instrument.

In aspects, the trocar mount is configured to rotate relative to the distal end portion of the rail between a first position and a second position. In the first position, the axis of the opening of the trocar mount is parallel with a longitudinal axis defined by the track of the rail and the housing portion of the surgical instrument is attachable to the instrument drive unit. In the second position, the axis of the opening of the trocar mount is disposed at a non-parallel angle relative to the longitudinal axis of the track of the rail and the housing portion of the surgical instrument is detached from the instrument drive unit.

In aspects, the surgical robotic system may further include a trocar having a head and a cannula extending distally from the head. The head may be configured for receipt in the opening of the trocar mount, such that the trocar rotates with the trocar mount. The cannula may be configured to receive the end effector of the surgical instrument.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
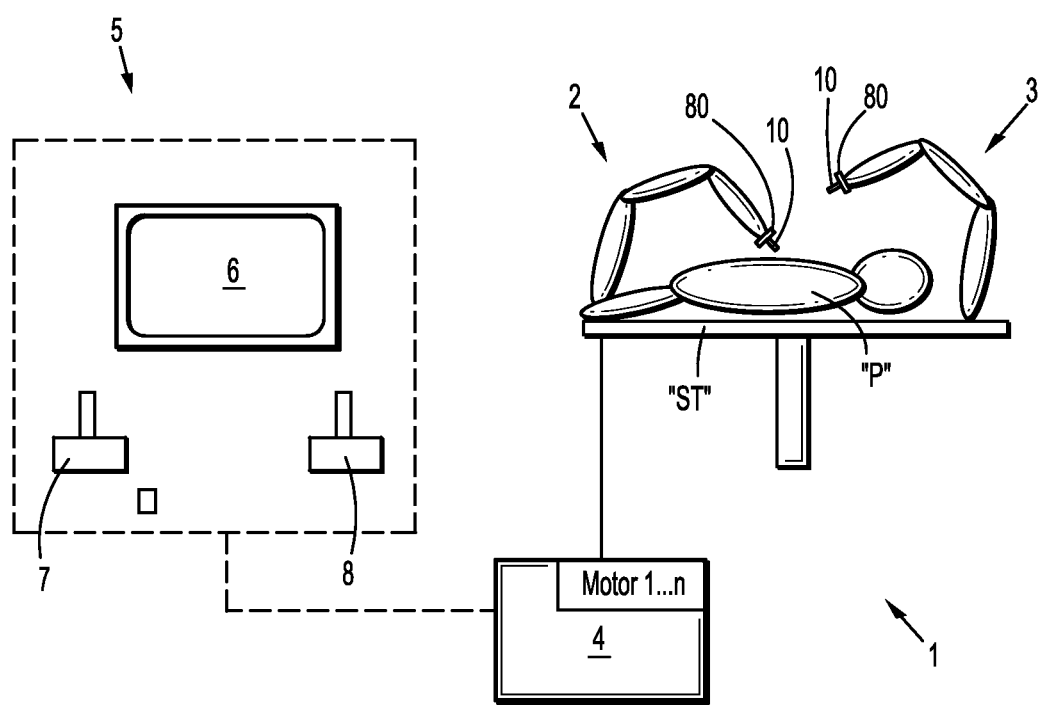
FIG. 1 is a schematic illustration of a robotic surgical system including a surgical robotic arm in accordance with the present disclosure.

Embodiments of the presently disclosed surgical robotic system are described in detail with reference to the drawings, in which like reference numerals designate identical or corresponding elements in each of the several views. As used herein the term "distal" refers to that portion of the robotic surgical system or component thereof, that is closer to a patient, while the term "proximal" refers to that portion of the robotic surgical system or component thereof, that is further from the patient.

As will be described in detail below, provided is a surgical robotic arm including a plurality of elongate members or links that are interconnected with one another and rotatable relative to one another. One of the links is a rail along which an instrument drive unit and an attached surgical instrument are configured to slide. The rail has a trocar mount rotatably coupled to a distal end portion thereof. The trocar mount supports a trocar or another suitable surgical access device that guides passage of the surgical instrument therethrough and into a surgical site. The trocar mount rotates relative to the rail between an in-use orientation, in which the trocar and the surgical instrument are coaxial with the instrument drive unit, and a loading/unloading orientation, in which the trocar and the surgical instrument are angled out of alignment with the instrument drive unit. By making the trocar mount rotatable, loading and unloading of the surgical instrument to and from the instrument drive unit is made possible without having to first proximally withdraw the distal-most end of the surgical instrument from the trocar. Since the instrument drive unit no longer has to be slid to its proximal limit in order to detach the surgical instrument therefrom, the rail may be provided with a shorter overall length, which improves patient bedside access, reduces the footprint of the surgical robotic system, and provides other advantages that may be apparent to one of ordinary skill in the art.

Referring initially to FIG. 1, a surgical system, such as, for example, a robotic surgical system 1, generally includes a plurality of surgical robotic arms 2, 3 having an instrument drive unit 80 and an electromechanical instrument 10 removably attached thereto; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints, as will be described in greater detail below. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 80, and thus electromechanical instrument 10 execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical instrument 10. Robotic surgical system 1 may also include more than two robotic arms 2, 3, the additional robotic arms likewise being connected to control device 4 and being telemanipulatable by means of operating console 5. A surgical instrument, for example, electromechanical surgical instrument 10, may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a motor, such as, for example, a hollow core motor, configured to drive a relative rotation of elongate members of surgical robotic arm 2.

For a detailed description of the construction and operation of a robotic surgical system, reference may be made to U.S. Pat. No. 8,828,023, entitled "Medical Workstation," the entire contents of which are incorporated by reference herein.

Figure 2:
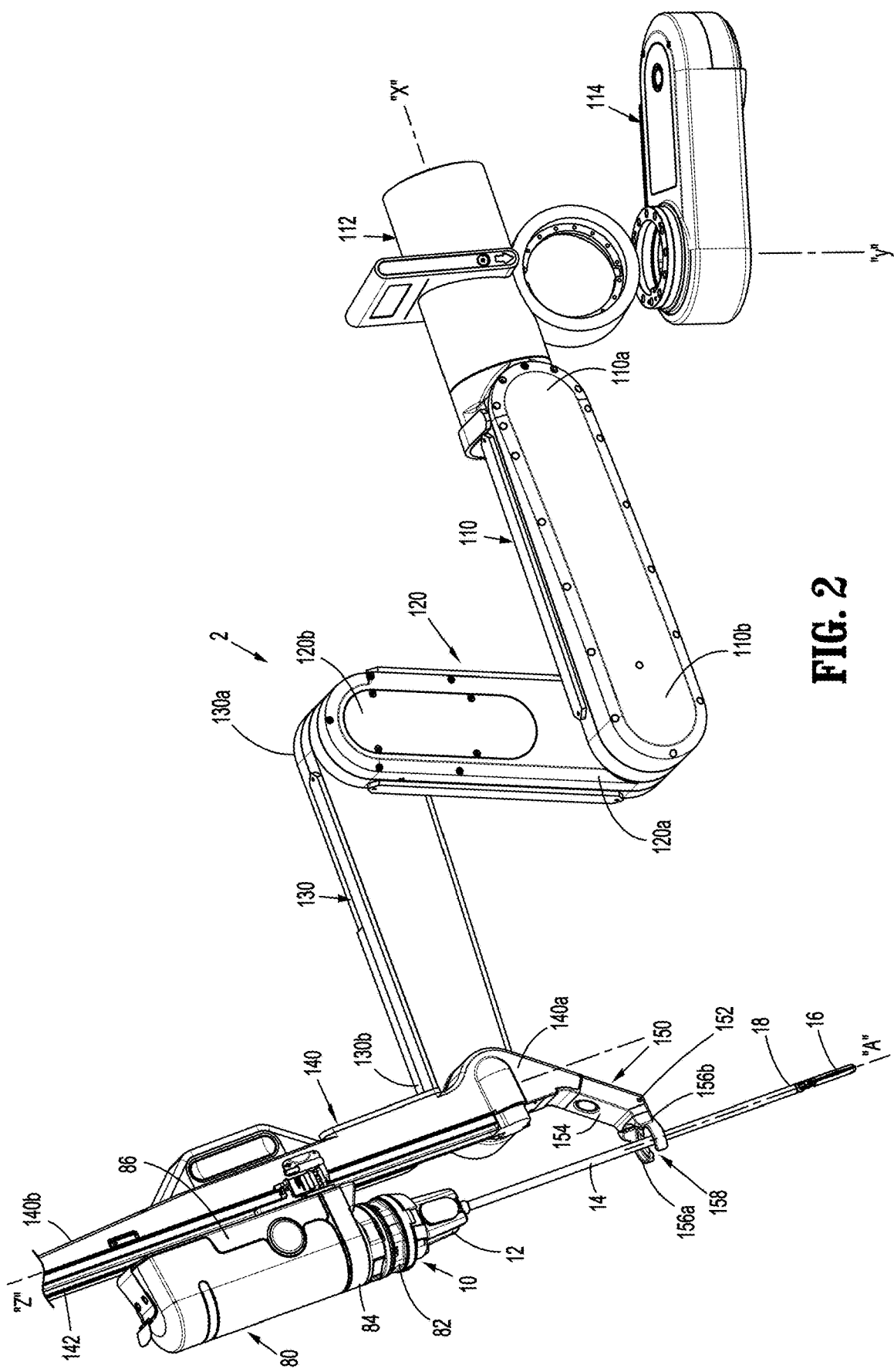
FIG. 2 is a side, perspective view of the surgical robotic arm of FIG. 1 coupled to a surgical instrument and a base.
Figure 3:
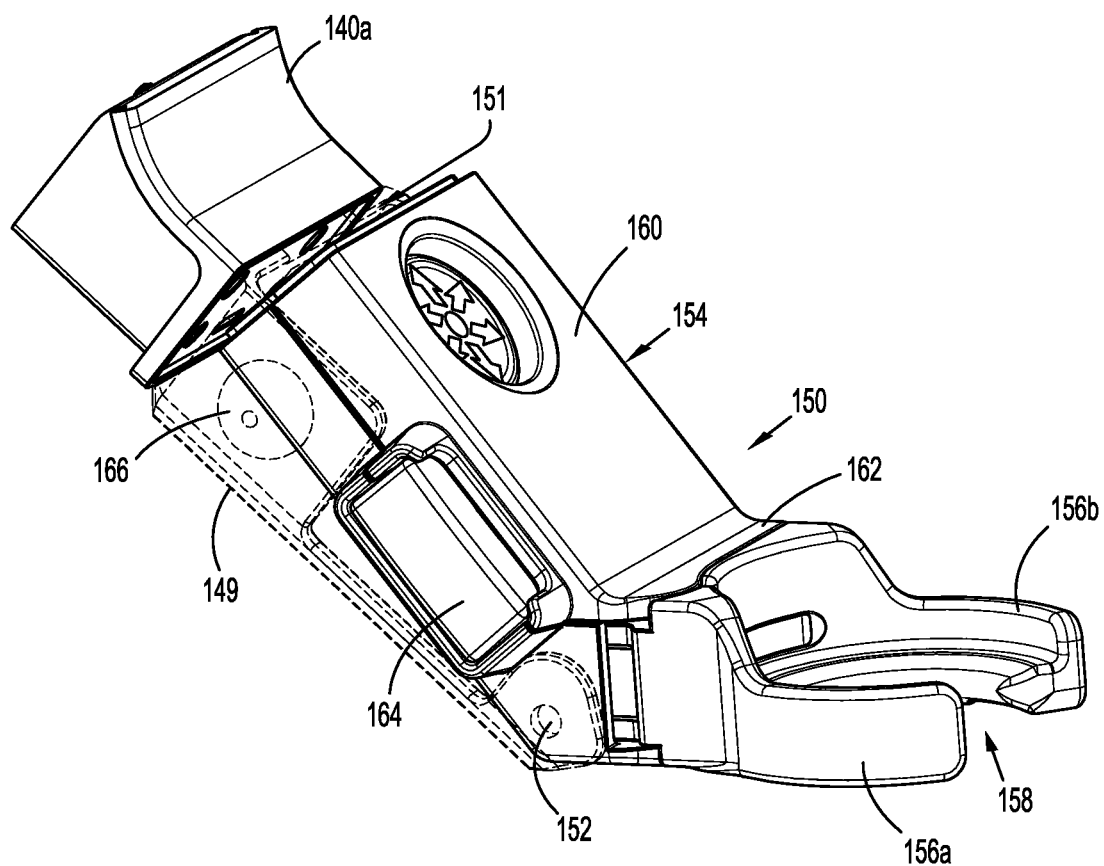
FIG. 3 is a side, perspective view of a trocar mount of the surgical robotic arm of FIG. 2.

With reference to FIG. 2, the surgical instrument 10 has a housing portion 12, an elongated shaft 14 extending distally from the housing portion 12, and an end effector 16 supported on a distal end portion 18 of the elongated shaft 14. The housing portion 12 has a proximal coupling mechanism 20 defining a ramped surface 22 (FIG. 5) configured for slidable engagement in a correspondingly configured sterile interface module 82, which couples the surgical instrument 10 to a distal end portion 84 of the instrument drive unit 80. In aspects, the housing portion 12 of the surgical instrument 10 may be detachably, drivingly coupled to the instrument drive unit 80 via other suitable fastening mechanisms, such as a snap-fit engagement, an interference fit, a threaded engagement, etc.

The surgical robotic arm 2 includes a plurality of elongate members or links 110, 120, 130 pivotably connected to one another to provide varying degrees of freedom to the robotic arm 2. In particular, the robotic arm 2 includes a first elongate member 110, a second elongate member 120, a third elongate member 130, and a fourth elongate member or rail 140. The first elongate member 110 has a first end 110a and a second end 110b. The first end 110a is rotatably coupled to a connector 112. The connector 112 is rotatably coupled to a fixed surface or base 114, for example, a surgical cart, a surgical table, stanchion, gantry, operating room wall or ceiling, or other surface present in the operating room. The first end 110a of the first elongate member 110 is rotatable relative to the connector 112 about a longitudinal axis "X," and the connector 112 is swivelable (or pivotable, rotatable, or articulatable) relative to the base 114 about a swivel axis "Y" that is perpendicular relative to the longitudinal axis "X" of the connector 112. The second end 110b of the first elongate member 110 is coupled to a first end 120a of the second elongate member 120 and configured to rotate relative to the first elongate member 110 about a pivot axis defined through the second end 110b of the first elongate member 110 and the first end 120a of the second elongate member 120. The third elongate member 130 includes a first end 130a rotatably coupled to the second end 120b of the second elongate member 120, and a second end 130b.

It is contemplated that the robotic arm 2 has a plurality of motors, such as, for example, hollow core or pancake motors (not shown) disposed at each of the joints for driving the relative rotation of the elongate members 110, 120, 130. A motor (not shown) may also be provided in the connector 112 for driving a rotation of the first elongate member 110 relative to the connector 112, and a motor (not shown) may be provided in the base 114 for driving the swivel motion of the connector 112, along with the attached robotic arm 2, relative to the base 114.

The rail 140 of the robotic arm 2 has a first end portion or distal end portion 140a rotatably coupled to the second end 130b of the third elongate member 130, a second end portion or proximal end portion 140b, and a track 142 defined between the first and second end portions 140a, 140b. The track 142 is configured for slidable attachment of the instrument drive unit 80, such that the surgical instrument 10 and instrument drive unit 80 are configured to slide as one unit along a longitudinal axis "Z" defined by the track 142. The instrument drive unit 80 may be slidably coupled to the track 142 via a carriage 86 that slides along the track 142 upon a selective actuation by motor(s) (not shown) supported on the rail 140 or motors (1 . . . n) of the control device 4 (FIG. 1). As such, the surgical instrument 10 can be moved to a selected position along the rail 140 when attached to the instrument drive unit 80.

Figure 4A:
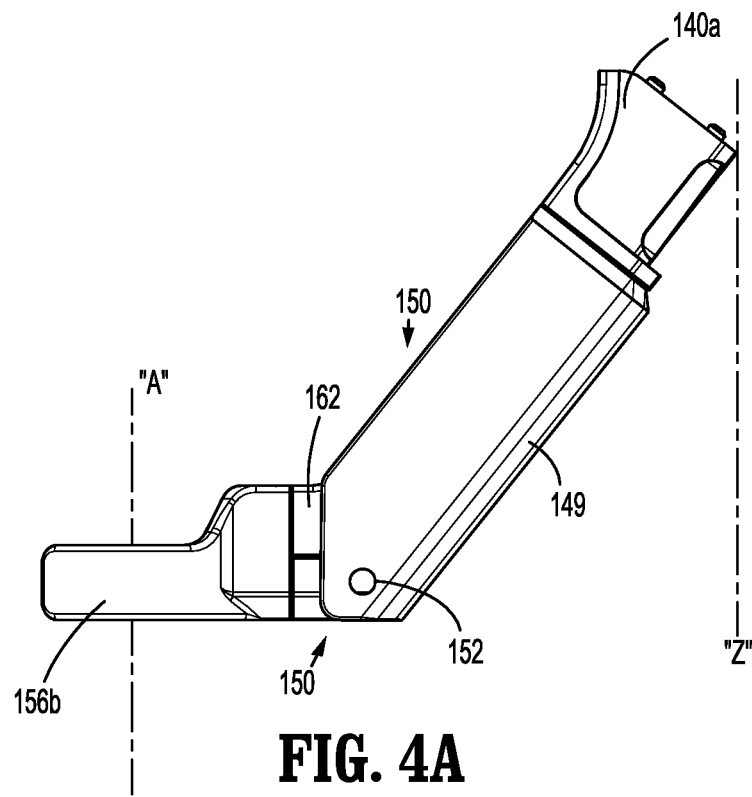
FIG. 4A is a side view illustrating the trocar mount of FIG. 3 in a first rotational orientation relative to a rail of the surgical robotic arm.
Figure 4B:
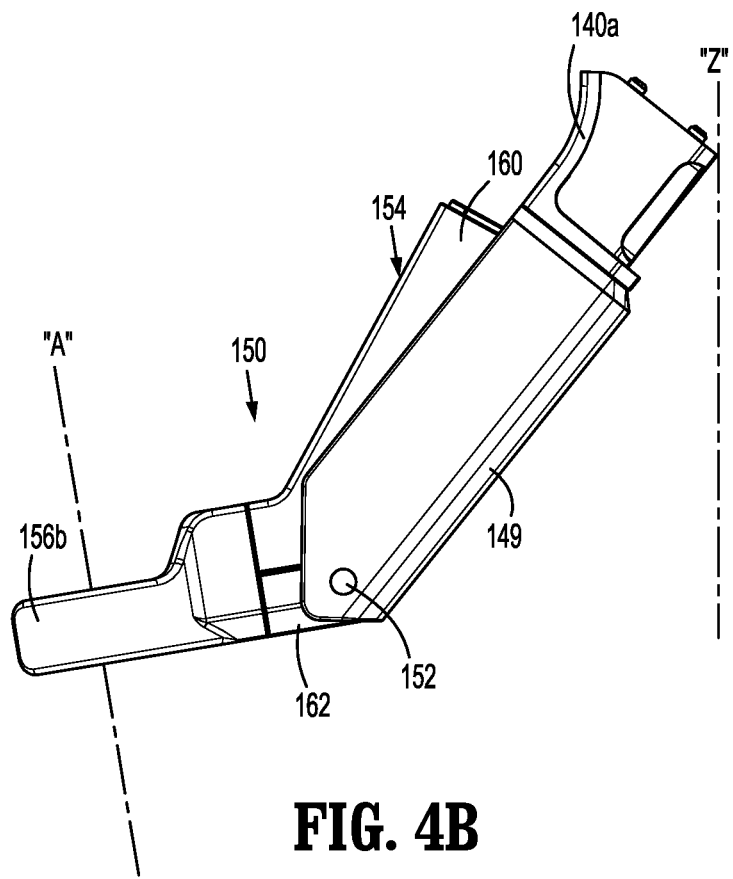
FIG. 4B is a side view illustrating the trocar mount in a second rotational orientation relative to the rail.
Figure 5:
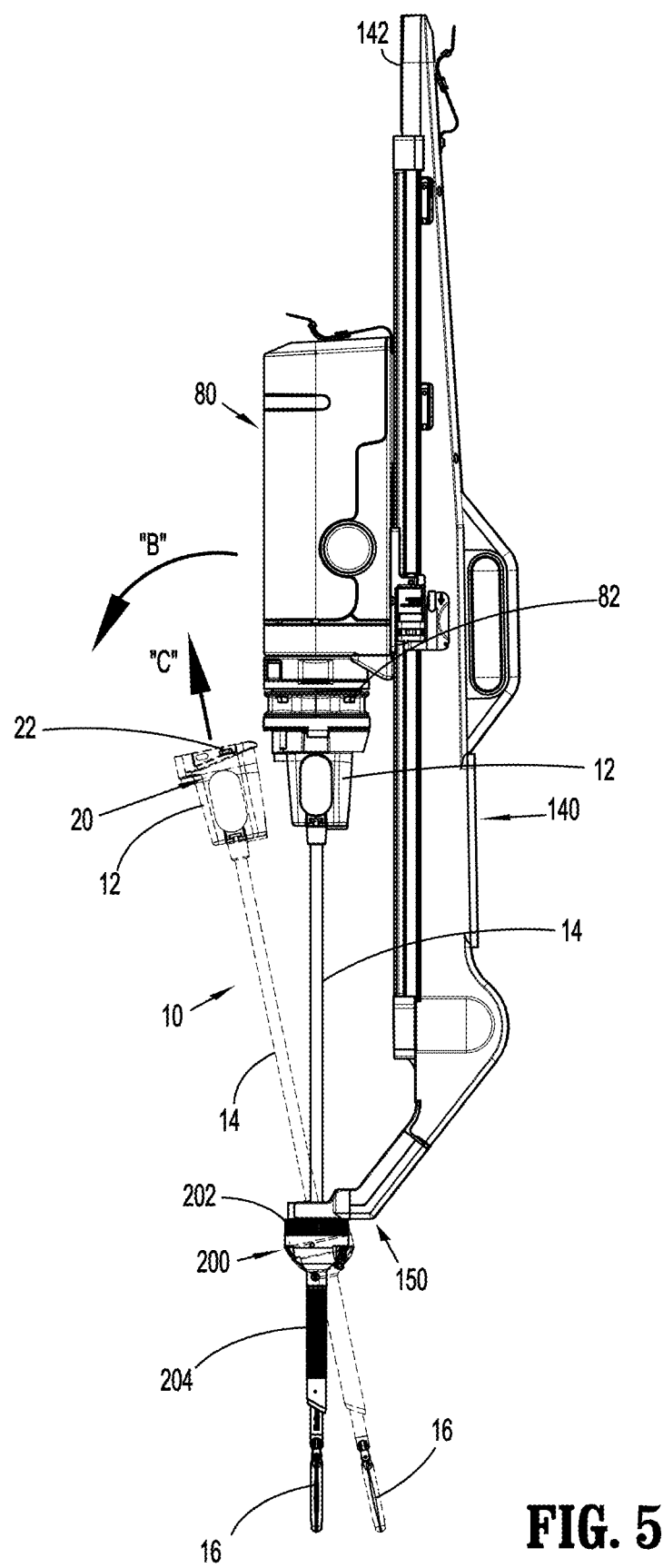
FIG. 5 is a side view illustrating the surgical instrument of FIG. 2 in a loaded position, and an unloaded position (shown in phantom).

With reference to FIGS. 2-4B, the rail 140 of the surgical robotic arm 2 further includes a trocar mount 150 rotatably coupled to the first end portion 140a of the rail 140 via a pivotable connection point 152. The trocar mount 150 includes a back member 154 and a pair of clamp arms 156a, 156b coupled to the back member 154. The clamp arms 156a, 156b together define an opening 158 configured for receipt and selective capture of a head 202 of a trocar 200 (FIG. 5). In aspects, the clamp arms 156a, 156b may be pivotable relative to the back member 154 to adjust the diameter of the opening 158 to selectively fix the head 202 of the trocar 200 therebetween. The clamp members 156a, 156b may be arcuate such that opening 158 is annular and/or assume other suitable shapes. In aspects, the clamp arms 156a, 156b may connect at their ends to enclose the opening 158.

The back member 154 of the trocar mount 150 has a body member 160 pivotably coupled to a bracket 149 that extends from the first end portion 140a of the rail 140. The body member 160 is pivotably coupled to the bracket 149 via the pivotal connection point 152 (e.g., a pin and hole connection). The back member 154 is pivotable relative to the bracket 149 of the rail 140 to adjust the position of the opening 158 of the clamp arms 156a, 156b by about 5 degrees to about 25 degrees, and in some aspects by about 10 degrees. The back member 154 further includes a shank 162 extending from the body member 160 at an obtuse angle to orient the opening 158 of the clamp arms 156a, 156b in coaxial alignment with the instrument drive unit 80 and the surgical instrument 10. In aspects, the shank 162 may extend at any suitable angle relative to the body member 160, such as an acute angle or perpendicularly. The body member 160 of the back member 154 is movably received in a correspondingly-shaped pocket 151 defined in the bracket 149 of the rail 140.

The trocar mount 150 further includes a button 164 attached to a lateral side of the back member 154 and configured to move relative to the back member 154 between an unactuated position and an actuated position. In the unactuated position, the button 164 is configured to lock the trocar mount 150 in a first rotational orientation (FIG. 4A), and in the depressed or actuated position, the trocar mount 150 is free to rotate relative to the bracket 149 of the rail 140. The button 164 may be resiliently biased toward the unactuated position via a biasing member (e.g., a spring (not shown)). The button 164 is attached to a boss 166 (FIG. 3) of the trocar mount 150 that moves into and out of engagement with a recess (not explicitly shown) defined in the bracket 149. When the button 164 is in the unactuated position, the boss 166 is received in the recess of the bracket 149, whereby the engagement between the boss 166 and the bracket 149 resists rotation of the trocar mount 150 relative to the bracket 149. When the button 164 is moved to the actuated position (e.g., depressed), the boss 166 is moved out of the recess to permit rotation of the trocar mount 150 relative to the bracket 149. Other mechanisms for selectively fixing the trocar mount 150 in the first rotational orientation are also contemplated.

With reference to FIG. 5, the surgical robotic system 1 may further include the trocar 200 for guiding the end effector 16 of the surgical instrument 10 through a natural or artificial opening in a patient and into a surgical site. The trocar 200 generally includes the head 202 and a cannula 204 extending distally from the head 202. The cannula 204 is configured to receive the end effector 16 of the surgical instrument 10.

In operation, to exchange the surgical instrument 10 or otherwise detach/attach the surgical instrument 10 from the instrument drive unit 80, the instrument drive unit 80 may be moved proximally along the track 142 of the rail 140 to move the end effector 16 out of the surgical site. In aspects, adjustment of the axial position of the instrument drive unit 80 may not need to be a step in the process of attaching/detaching the surgical instrument 10 from the instrument drive unit 80.

The button 164 of the trocar mount 150 is actuated to unlock the trocar mount 150 from the bracket 149 of the rail 140. With the button 164 in the actuated position, the trocar mount 150 may be rotated relative to the rail 140 out of the in-use or first rotational orientation, in which an axis "A" (FIG. 4A) defined by the opening 158 of the trocar mount 150 is parallel with the longitudinal axis "Z" defined by the track 142 of the rail 140, toward a second rotational orientation (FIG. 4B). In the second rotational orientation, the axis "A" of the opening 158 of the trocar mount 150 is disposed at a non-parallel angle (e.g., about 10 degrees) relative to the longitudinal axis "Z" of the track 142 of the rail 140.

When the trocar mount 150 is rotated, in the direction indicated by arrow "B" in FIG. 5, out of the first rotational orientation (FIG. 4A) toward the second rotational orientation (FIG. 4B), the trocar 200 rotates therewith along with the surgical instrument 10 due to the elongated shaft 14 of the surgical instrument 10 being disposed within the trocar 200. As the surgical instrument 10 is being rotated, the housing portion 12 of the surgical instrument 10 slides out of engagement with the sterile interface module 82, thereby detaching the surgical instrument 10 from the instrument drive unit 80. With the surgical instrument 10 detached from the instrument drive unit 80 and no longer aligned with the instrument drive unit 80, the surgical instrument 10 may be manually slid in a generally proximal direction "C" completely out of the trocar 200.

After having detached the surgical instrument 10 from the robotic arm 2, a second, sterile surgical instrument 10 may be attached to the instrument drive unit 80 by first inserting the end effector 16 of the second surgical instrument 10 into the trocar 200 a sufficient distance such that the housing portion 12 of the second surgical instrument 10 is in side-by-side relation with the sterile interface module 82. The trocar mount 150 may be rotated back to the first rotational orientation, whereby the trocar 200 and the second surgical instrument 10 are also rotated. The housing portion 12 of the surgical instrument 10 rotates into mating engagement with the distal coupling mechanism/sterile interface module 82 of the instrument drive unit 80. Upon rotating the trocar mount 150 to the first rotational orientation, the button 164 thereof may automatically lock the trocar mount 150 to hold the trocar 200 in vertical registration with the instrument drive unit 80.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical robotic arm for use in a minimally invasive surgical procedure, comprising:
   a plurality of elongate members movably coupled to one another;
   an elongated rail pivotably coupled to at least one of the plurality of elongate members, the rail having a proximal end portion, a distal end portion, and a track defined between the proximal and distal end portions and configured for slidable engagement of a surgical instrument thereto, the track of the rail defining a longitudinal axis; and
   a trocar mount pivotably supported at the distal end portion of the rail, the trocar mount defining an opening configured to receive at least one of a trocar or an elongated shaft of the surgical instrument, wherein the opening of the trocar mount defines an opening axis therethrough along which the surgical instrument is configured to translate, wherein the trocar mount is configured to pivot about a pivot axis extending orthogonal to each of the longitudinal axis and the opening axis, wherein the pivot axis is located between the longitudinal axis and the opening axis, and wherein the pivot axis is spaced a distance from each of the longitudinal axis and the opening axis.

2. The surgical robotic arm according to claim 1, wherein the trocar mount is configured to pivot relative to the distal end portion of the rail between a first position, in which the opening axis of the opening of the trocar mount is parallel to the longitudinal axis defined by the track of the rail, and a second position, in which the opening axis of the opening of the trocar mount is disposed at a non-parallel angle relative to the longitudinal axis of the track of the rail.

3. The surgical robotic arm according to claim 2, wherein the trocar mount includes:
   a back member; and
   a pair of clamp arms extending from the back member, the pair of clamp arms together defining the opening of the trocar mount.

4. The surgical robotic arm according to claim 3, wherein the trocar mount further includes a button attached to the back member and configured to move between an unactuated position, in which the button locks the trocar mount in the first position, and an actuated position, in which the trocar mount is free to rotate relative to the distal end portion of the rail.

5. The surgical robotic arm according to claim 4, wherein the button is resiliently biased toward the unactuated position.

6. The surgical robotic arm according to claim 3, wherein the distal end portion of the rail defines a pocket having the back member of the trocar member movably received therein.

7. The surgical robotic arm according to claim 3, wherein the back member of the trocar mount is pivotably coupled to the distal end portion of the rail.

8. The surgical robotic arm according to claim 3, further comprising a bracket connected to the rail, the bracket extending along the longitudinal axis, wherein the trocar mount is pivotably connected to the bracket, and wherein the bracket defines a pocket configured to receive the back member of the trocar mount when the trocar mount is in the first position.

9. The surgical robotic arm according to claim 1, wherein the plurality of elongate members includes:
   a first elongate member having a first end and a second end;
   a second elongate member having a first end rotatably connected to the second end of the first elongate member, and a second end; and
   a third elongate member having a first end rotatably connected to the second end of the second elongate member, and a second end, the distal end portion of the rail being rotatably coupled to the second end of the third elongate member.

10. A surgical robotic system, comprising:
    an elongated rail having a proximal end portion, a distal end portion, and a track defined between the proximal and distal end portions, the track of the rail defining a longitudinal axis;
    an instrument drive unit configured for slidable engagement with the track of the rail;
    a surgical instrument including:
       a housing portion configured to detachably connect to the instrument drive unit;
       an elongate shaft extending distally from the housing portion; and an end effector coupled to a distal end portion of the elongate shaft, the instrument drive unit being configured to drive an operation of the end effector of the surgical instrument; and a trocar mount pivotably coupled to the distal end portion of the rail, the trocar mount defining an opening configured to receive the elongate shaft of the surgical instrument, wherein the opening of the trocar mount defines an opening axis therethrough along which the surgical instrument is configured to translate, wherein the trocar mount is configured to pivot about a pivot axis extending orthogonal to each of the longitudinal axis and the opening axis, wherein the pivot axis is located between the longitudinal axis and the opening axis, and wherein the pivot axis is spaced a distance from each of the longitudinal axis and the opening axis.

11. The surgical robotic system according to claim 10, wherein the trocar mount is configured to pivot relative to the distal end portion of the rail between a first position, in which the opening axis of the opening of the trocar mount is parallel to the longitudinal axis defined by the track of the rail and the housing portion of the surgical instrument is attachable to the instrument drive unit, and a second position, in which the opening axis of the opening of the trocar mount is disposed at a non-parallel angle relative to the longitudinal axis of the track of the rail and the housing portion of the surgical instrument is detached from the instrument drive unit.

12. The surgical robotic system according to claim 11, wherein the trocar mount includes:
 a back member; and
 a pair of clamp arms extending from the back member, the pair of clamp arms together defining the opening of the trocar mount.

13. The surgical robotic system according to claim 12, wherein the trocar mount further includes a button attached to the back member and configured to move between an unactuated position, in which the button locks the trocar mount in the first position, and an actuated position, in which the trocar mount is free to rotate relative to the distal end portion of the rail.

14. The surgical robotic system according to claim 13, wherein the button is resiliently biased toward the unactuated position.

15. The surgical robotic system according to claim 12, wherein the distal end portion of the rail defines a pocket having the back member of the trocar member movably received therein.

16. The surgical robotic system according to claim 12, wherein the back member of the trocar mount is pivotably coupled to the distal end portion of the rail.

17. The surgical robotic system according to claim 10, further comprising a trocar including:
 a head configured for receipt in the opening of the trocar mount, such that the trocar rotates with the trocar mount; and
 a cannula extending distally from the head and configured to receive the end effector of the surgical instrument.

18. A surgical robotic system, comprising:
an elongated rail having a proximal end portion, a distal end portion, and a track defined between the proximal and distal end portions, the track of the rail defining a longitudinal axis;
an instrument drive unit configured for slidable engagement with the track of the rail;
a surgical instrument including:
 a housing portion configured to detachably connect to the instrument drive unit;
 an elongate shaft extending distally from the housing portion; and
 an end effector coupled to a distal end portion of the elongate shaft, the instrument drive unit being configured to drive an operation of the end effector of the surgical instrument;
a trocar mount pivotably coupled to the distal end portion of the rail, the trocar mount defining an opening configured to receive the elongate shaft of the surgical instrument, wherein the opening of the trocar mount defines an opening axis therethrough along which the surgical instrument is configured to translate, wherein the trocar mount is configured to pivot about a pivot axis extending orthogonal to each of the longitudinal axis and the opening axis, and wherein the pivot axis is located between the longitudinal axis and the opening axis; wherein the trocar mount is configured to pivot relative to the distal end portion of the rail between:
 a first position, in which the opening axis of the opening of the trocar mount is parallel to the longitudinal axis defined by the track of the rail and the housing portion of the surgical instrument is attachable to the instrument drive unit; and
 a second position, in which the opening axis of the opening of the trocar mount is disposed at a non-parallel angle relative to the longitudinal axis of the track of the rail and the housing portion of the surgical instrument is detached from the instrument drive unit;
wherein the trocar mount includes:
 a back member; and
 a pair of clamp arms extending from the back member, the pair of clamp arms together defining the opening of the trocar mount; and
a bracket connected to the rail, the bracket extending along the longitudinal axis, wherein the trocar mount is pivotably connected to the bracket, and wherein the bracket defines a pocket configured to receive the back member of the trocar mount when the trocar mount is in the first position.

\* \* \* \* \*